US006441038B1

(12) United States Patent
Loder et al.

(10) Patent No.: US 6,441,038 B1
(45) Date of Patent: Aug. 27, 2002

(54) TREATMENT OF FATIGUE, HEAD INJURY AND STROKE

(75) Inventors: Cari Loder, Farncombe; David F. Horrobin, Stirling, both of (GB)

(73) Assignee: Laxdale Limited, Sterling (GB)

( * ) Notice: Subject to any disclaimer, the term of this patent is extended or adjusted under 35 U.S.C. 154(b) by 0 days.

(21) Appl. No.: 09/686,629

(22) Filed: Oct. 12, 2000

(30) Foreign Application Priority Data

Oct. 12, 1999 (GB) .............................................. 9924172

(51) Int. Cl.$^7$ ........................................... A61K 31/195

(52) U.S. Cl. .................... 514/561; 514/217; 514/239.2; 514/438; 514/613; 514/649

(58) Field of Search ................................ 514/561, 217, 514/239.2, 649, 438, 613

(56) References Cited

U.S. PATENT DOCUMENTS 4,431,670 A * 2/1984 Heller
6,096,737 A * 8/2000 Loder

FOREIGN PATENT DOCUMENTS

GB  2 297 868   8/1996
GB  2 309 774   8/1997

OTHER PUBLICATIONS

Merck Manual 15th edition, p. 1381, 1987.*
Gulick, E.E., "Model Conformation of the MS–Related Symptom Checklist", *Nursing Research*, 1989; 38:147–153.
Fisk, J.D. et al., "The Impact of Fatigue on Patients with Multiple Sclerosis", *The Canadian Journal of Neurological Sciences*, 1994; 21:9–14.
Moore, R.Y. and Bloom, F.E., "Central Catecholamine Neuron Systems: Anatomy and Physiology of the Norepinephrine and Epinephrine Systems" *Annual Review of Neuroscience* 1979; 2:113–168.
Smith, B.H. and Sweet, W.H. "Neuroscience for the neurosurgeon; Monoaminergic Regulation of Central Nervous System Function: I. Noradrenergic Systems", *Neurosurgery*, 1978; vol. 3, No. 1:109–119.
Ingles, J.L. et al. "Fatigue After Stroke", *Archives of Physical Medicine and Rehabilitation*, Feb. 1999; vol. 80, No. 2:173–177.
Boyeson, M.G. et al. "Sparing of Motor Function After Cortical Injury", *Archives of Neurology*, Apr. 1994:51:405–413.
Feeney, D.M. et al. "Noradrenergic Pharmacotherapy, Intracerebral Infusion and Adrenal Transplantation Promote Functional Recovery After Cortical Damage", *Journal of Neural Transplantation and Plasticity*, Jan.–Mar. 1993; vol. 4, No. 3:199–213.

Weiss, J.M. et al., "Behavioral Depression Produced By An Uncontrollable Stressor: Relationship to Norepinephrine, Dopamine, and Serotonin Levels in Various Regions of Rat Brain", *Brain Research Reviews*, Oct. 1981, vol. 3, No. 2:167–205.
Clauw, D.J. M.D. "Fibromyalgia: More Than Just a Musculoskeletal Disease" *American Family Physician*, Sep. 1, 1995; vol. 52, No. 3:843–851.
Glynn, C.J. et al.; "Role of Spinal Noradrenergic System In Transmission of Pain in Patients With Spinal Cord Injury", *The Lancet*, Nov. 29, 1986; vol. II, No. 8518:1249–51.
Reddy, S.V.R. et al., "Spinal Cord Pharmacology of Adrenergic Agonist–Mediated Antinociception", *The Journal of Pharmacology*, Jun., 1980; vol. 213, No. 3:525–533.
Feeney, et al.; "From Laboratory to Clinic: Noradrenergic Enhancement of Physical Therapy for Stroke or Trauma Patients", *Advances in Neurology*, 1997; vol. 73:383–394.
Boyeson, M.G. "Intraventricular Norepinephrine Facilities Motor Recovery Following Sensorimotor Cortex Injury", *Pharmacology Biochemistry and Behavior*, Mar. 1990; vol. 35, No. 3:497–501.
Boyeson, M.G. and Harmon, R., "Effects of Trazodone and Desipramine On Motor Recovery In Brain–Injured Rats", *American Journal of Physical Medicine and Rehabilitation*, Oct. 1993; vol. 72, No. 5:286–293.
R.J. Valentino et al. "Antidepressant Actions on Brain Noradrenergic Neurons", *The Journal of Pharmacology and Experimental Therapeutics*, May 1990; vol. 258, No. 2:833–840.
Boyeson, M.G. et al., "Comparative Effects of Fluoxetine, Amitriptyline and Serotonin on Functional Motor Recovery After Sensorimotor Cortex Injury", *American Journal of Physical Medicine & Rehabilitation*, Apr. 1994; vol. 73, No. 2:76–83.

(List continued on next page.)

*Primary Examiner*—Rebecca Cook
(74) *Attorney, Agent, or Firm*—Foley & Lardner

(57) ABSTRACT

A method of treatment of disorders of neurological origin and drug formulations for use in the method are disclosed. These conditions comprise fatigue and associated syndromes of pain, weakness and depressed mood which are associated with chronic fatigue syndrome, brain injury and stroke, stress, fibromyalgia, and irritable bowel syndrome. The treatment comprises administering to a patient in need thereof a selective inhibitor of noradrenaline reuptake combined with either phenylalanine or tyrosine in the same dosage form or the same pack.#

The noradrenergic drug may be selected from lofepramine, desipramine or reboxetine. The selective inhibitor may be a combined inhibitor of both noradrenaline and serotonin reuptake such as venlafaxine, duloxetine or milnacipran, or an inhibitor of both noradrenaline and dopamine reuptake such as bupropion.

12 Claims, No Drawings

OTHER PUBLICATIONS

Milner, J.D. and Wurtman, R.J., "Catecholamine Synthesis: Physiological Coupling To Precursor Supply", *Biochemical Pharmacology*, Mar. 15, 1986; vol. 35, No. 6:875–881.

Bolden–Watson, C. and Richelson, E., "Blockade By Newly–Developed Antidepressants of Biogenic Amine Uptake Into Rat Brain Synaptosomes", *Life Sciences*, Nov. 1993; vol. 52, No. 12:1023–1029.

Sanchez C. and Hyttel, J. "Comparison of the Effects of Antidepressants and Their Metabolites on Reuptake of Biogenic Amines and on Receptor Binding", *Cellular and Molecular Neurobiology*, Aug. 1999; vol. 19, No. 4:467–489.

* cited by examiner

TREATMENT OF FATIGUE, HEAD INJURY AND STROKE

The present application claims priority to United Kingdom patent application 9924172.1, filed Oct. 12, 1999.

FIELD OF THE INVENTION

This invention relates to the treatment of neurological disorders and more particularly to the treatment of neurologically-related fatigue, brain injury, stress, and related conditions.

BACKGROUND OF THE INVENTION

Some years ago one of us noted that combinations of various types of antidepressants, together with neurotransmitter precursors such as phenylalanine, tyrosine and tryptophan, could improve the symptoms of multiple sclerosis and a patent application covering this invention was filed (PCT/GB95/02361). Subsequently we and various associates also noticed that these same combinations could improve peripheral neuropathy, pain from peripheral neuropathy and pain of any type (PCT/GB97/01822 and PCT/GB97/02295). In each case vitamin B12, folic acid, pyridoxine and other nutrients could be added to the formulations.

SUMMARY OF THE INVENTION

We have continued to make clinical observations on the effects of various drugs and amino acids on multiple sclerosis and on pain and as a result have made new discoveries which extend the inventions disclosed in the above patent applications. In particular, we have found that the range of drugs and amino acid precursors which are most effective are those which specifically affect noradrenaline at nerve endings so activating noradrenergic systems, such as lofepramine, desipramine and reboxetine among the drugs and phenylalanine and tyrosine among the amino acids. Phenylanine and tyrosine are precursors of noradrenaline. Tryptophan, the serotonin precursor, and drugs which act prefentially on serotonin have some actions but are less effective. Other drugs which are effective in combination with phenylalanine or tyrosine are drugs which are combined inhibitors of both noradrenaline and serotonin uptake, such as venlafaxine, duloxetine or milnacipran, and drugs which are combined inhibitors of both dopamine and noradrenaline reuptake such as bupropion.

In addition to refining the list of the most effective drugs, the list of possible uses of the combinations has been expanded to include chronic stress, chronic fatigue syndrome, fibromyalgia, fatigue in association with migraine, fatigue in association with brain injuries or other forms of brain damage including stroke, and illnesses associated with chronic fatigue such as irritable bowel syndrome, and brain infections with any agent including viruses, prions or bacteria. A particularly important new use for the combinations of noradrenergic drug and noradrenaline precursor is the neurological rehabilitation of patients after any form of damage to the brain, including traumatic brain injuries and strokes.

DETAILED DESCRIPTION

Because of the anecdotal evidence of the benefits of lofepramine and phenylalanine, reported in earlier patent applications, we have conducted a substantial, randomised, placebo-controlled, double blind trial in 138 patients with multiple sclerosis (MS). Half the patients received 70 mg lofepramine and 500mg I-phenylalanine twice a day, while the other half received identical-appearing placebos. All patients in both groups received regular injections of vitamin B12. 44 patients had the relapsing/remitting type of MS, 35 had primary progressive disease, and 59 had secondary progressive disease. A wide range of disease severeites was exhibited by the patients: on the Kurtzke Extended Disability Symptom Scale (EDSS) about half the patients had seventies of 6.5 or more, with the other half 6.0 or less. Patients were assessed on various scales, but particularly the Kurtzke scale, and the Gulick MS Patient Symptom scale. The Kurtzke scale aims to provide a relatively objective assessment of the degree of disability as assessed by the neurologist. The Gulick scale assesses a range of symptoms assessed by the patient. These symptoms can be grouped into six factors (Gulick E E, Model confirmation of the MS-related symptom checklist. Nursing Res 1989; 38: 147–153): musculoskeletal (including weakness, spasms and balance problems): elimination (bowel and bladder): emotions (depression, anxiety and loneliness): sensory (pain, numbness, paraesthesia): head symptoms (visual, swallowing and memory): and fatigue. The trial lasted for six months and patients were assessed at baseline, 2 weeks, 4 weeks, 3 months and 6 months.

The results were clear cut and surprising and showed the best evidence ever obtained for a treatment for MS, especially given the relatively short duration of the trial. Interferons slow down the rate of deterioration in MS but do not produce any actual improvements in symptoms. As a result trials have to be two or three years long in order to show differences between active and placebo groups: those differences depend not on improvement in the interferon group but on deterioration in the placebo group. In contrast, lofepramine + phenylalanine produced actual improvements both on the Gulick and the Kurtzke scales. The placebo group showed a deterioration in the Kurtzke scale, and a small improvement on the Gulick scale. The results are summarised in table 1.

Table 1. The results of the trial for the Kurtzke disability and Gulick symptom scales. In the change from baseline line, a + sign indicates improvement and a − sign indicates deterioration. In the difference between the two groups, a + sign indicates that active treatment with lofepramine and phenylalanine was better than placebo. There were 69 patients in each group.

| Parameter | Kurtzke | Gulick |
| --- | --- | --- |
| Baseline score | 6.07 | 20.02 |
| Change from baseline on active | +0.107 | +10.63 |
| Change from baseline on placebo | −0.132 | +3.68 |
| Difference between active and placebo | +0.239 | +6.95 |
| P for difference | 0.042 | 0.017 |

Three particularly surprising and striking findings emerged from the results obtained with the Gulick scale. First, the effect was very rapid: there was a clear difference between active and placebo by 2 weeks, which reached a peak at 4 weeks and then stayed stable for the remaining five months of the trial. Second, the improvement was seen across all the sub-scales of the Gulick scale (overall 20.5% from baseline, musculoskeletal 15%, elimination 27%, emotions 31%, sensory 23%, head 27% and fatigue 21%): these are large and important effects which have a major impact on the quality of life of patients. Third, the effect on fatigue was particularly important to the patients since it was quick, substantial and a contrast to the interferons which often increase fatigue initially. Patients with MS consistently state that fatigue is the single most important symptom which affects their quality of life (J D Fisk et al. The impact of fatigue on patients with multiple sclerosis. Canadian Journal of Neurological Science 1994; 21: 9–14). We had previously noted an effect on fatigue in a few patients with MS (PCT/GB95/02361) but had not drawn particular attention to this, nor claimed treatment of fatigue, nor expected to see such a large, consistent and statistically significant effect on this important and difficult to manage symptom.

The anecdotal evidence indicating that noradrenaline precursors and noradrenergic drugs like lofepramine and desipramine are particularly effective, and the new and unexpected clinical trial evidence which clearly proves the efficacy, and shows that the effect on fatigue is very important, and that the effects on symptoms are astonishingly rapid and effective across all the symptom groups, has led us to extend our ideas and new applications of those ideas. In particular, the combination of the noradrenaline precursors, phenylalanine and tyrosine, coupled with a drug which either has as its sole action or a component of its action the inhibition of noradrenaline reuptake, is now seen to be valuable in the treatment of fatigue in any form, in the management of rehabilitation after stroke, in the treatment of stress in any form, and in the treatment of fibromyalgia and related disorders such as irritable bowel syndrome.

We can now, as a result of these entirely novel clinical trial findings, draw conclusions about mechanisms of action which lead to these novel applications. First, it is apparent that the system involved is dependent on noradrenaline and to a much smaller extent on serotonin: the greater impact of noradrenergic as opposed to serotoninergic drugs, and the greater effect of phenylalanine as opposed to tryptophan, indicate this. Second, the mechanism is extremely rapid and is too quick to involve any major neuroregeneration which is likely to take months or years if it occurs: the mechanism is therefore likely to involve changes in the function of an existing neuronal system within the brain and spinal cord. Third, the wide range of systems improved by the treatment includes neuronal systems supplying the head and neck, the skeletal muscles, the sensory system, the autonomic nervous system and higher cortical functions: the nerve cells involved in the therapeutic effect must therefore interact with almost all parts of the brain and spinal cord.

What parts of the central nervous system might fulfil the criteria required to explain the effects of lofepramine and phenylalanine? There are two closely related systems which precisely fit our entirely novel and unexpected observations. These are the Locus Coeruleus (LC) and the Lateral Tegmentum (LT) (R Y Moore and F E Bloom, Central catecholamine neuron systems: anatomy and physiology of the norepinephrine and epinephrine systems. Annual Review of Neuroscience 1979; 2: 113–168. B H Smith and W H Sweet, Monoaminergic regulation of central nervous system function: I. Noradrenergic systems. Neurosurgery 1978; 3: 109–119).

The LT and the LC are unique systems. They are both dependent on noradrenaline (NA, also known as norepinephrine) as their main neurotransmitter. The LC is a neuronal nucleus located in the brainstem reticular formation. The LT is a more diffuse system including a number of nuclei such as the dorsal motor vagus, the nucleus tractus solitarius and adjacent tegmentum, and the lateral tegmentum itself. The nerve fibres of the LC travel virtually throughout the whole central nervous system, including to the spinal cord, brainstem, cerebellum, thalamus, hypothalamus, basal telencephalon and the entire cortex. The LT neurons are somewhat less widely distributed but even so go to the spinal cord, brainstem, hypothalamus and basal telencephalon.

The real peculiarity of these systems, however, relates to (a) their astonishingly frequent neuronal branching so that a single LT or LC nerve cell may have axons which connect with millions of other nerve cells, (b) the diverse endings of branches from a single nerve cell so that one branch may go to the cerebellum, for example, while another goes to the cortex, (c) their lack of clear cut synaptic end targets, with each nerve cell making diffuse contact with millions of other cells, and (d) their release of noradrenaline from sites along all the branches of the axons and not just from the synaptic endings. Smith and Sweet vividly state "single axons may traverse several regions of the brain, making no specific synaptic connections in any one area, but spraying transmitter (noradrenaline) over several areas".

The axons of the LT and LC systems are very widely distributed, making contact with motor nerve systems, sensory nerve systems, pain systems and autonomic systems such as those regulating cardiovascular and respiratory functions, bladder and bowel functions, reproductive functions and stress responses.

It is therefore apparent that the LT and LC systems are primarily noradrenergic systems which are able to influence almost all parts of the rest of the nervous system simultaneously. They are thus very strong candidates for the rapid and completely generalised relief of symptoms obtained in response to lofepramine and phenylalanine in the trial we have just completed in MS.

One of the well-known and difficult to explain observations in MS is that the symptoms seen in the patients are often poorly correlated with the precise positions of the lesions in the central nervous system which are identified by magnetic resonance imaging. Some of the symptoms can be directly related to the lesions, but many of the more generalised symptoms and especially the autonomic symptoms and the fatigue are difficult to relate precisely to the specific points of damage. This situation is similar to that seen in a substantial number of other central nervous system (CNS) disorders. In stroke, head injury, or any form of specific localised damage to the brain, it has long been recognised that there are two syndromes: the first is localised and clearly related to the specific nerve cells damaged by the lesion: the second is much more generalised and includes widespread impairment of neuronal function and very frequently includes substantial subjective fatigue (J L Ingles et al, Fatigue after stroke, Archives of Physical Medicine and Rehabilitation 1999; 80: 173–177. M G Boyeson et al. Sparing of motor function after cortical injury. Archives of Neurology 1994; 51: 405–413. D M Feeney et al, Noradrenergic pharmacotherapy, intracerebral infusion and adrenal transplantation promote functional recovery after cortical damage. Journal of Neural Transplantation and Plasticity 1993; 4: 199–213.). These syndromes are in many ways similar to those which occur in response to prolonged and uncontrollable stress, and also in the rather mysterious syndrome known as chronic fatigue syndrome which is closely related to fibromyalgia and which is associated with a number of other medical conditions including irritable bowel syndrome, and esophageal reflux and related disorders (J M Weiss et al, Behavioral depression produced by an uncontrollable stressor: relationship to norepinephrine, dopamine and serotonin levels in various regions of rat brain. Brain Research Reviews 1981; 3: 167–205. D J Clauw, Fibromyalgia: more than just a musculoskeletal disease. American Family Physician 1995; 52: 843–851).

In all of these conditions there is emerging evidence that the LC and LT systems are dysfunctional. The reasons for the dysfunction may be various. Because the LT and LC neurons go almost everywhere in the CNS, local damage to any part of the CNS will inevitably damage some axons from LT and LC nerve cells. That damage may then impair the function of the LC and LT themselves, or at the least impair the function of the other parts of the brain innervated by the damaged nerves. For example, many LC neurons have branches going to both the cerebellum and the cerebral cortex. A stroke or injury or an MS lesion affecting the cerebellum may thus alter cortical function and vice versa. Because the LT and LC neurons are an important part of the response to stress, sustained stress may lead to damage to or temporary or permanent exhaustion of the system. Viral infection may damage the LT and LC systems directly and this, with chronic stress, may be related to some chronic fatigue and fibromyalgia syndromes.

We propose that what lofepramine and phenylalanine are doing is activating the LC and LT system. This explains the effects on fatigue and on the whole range of symptoms in MS, involving motor, sensory, autonomic and higher cerebral functions. Activation of the LC and LT systems also explains the relief of pain of all types since the LC and LT noradrenergic systems are particularly involved in the regulation of chronic pain (eg C J Glynn et al, Role of spinal noradrenergic system in transmission of pain in patients with spinal cord injury, Lancet 1986; ii: 1249–51. S V R Reddy et al. Spinal cord pharmacology of adrenergic agonist-mediated antinociception. Journal of Pharmacology and Experimental Therapeutics 1980; 213: 525–533). This mechanism indicates that the treatment will also be effective in chronic stress, chronic fatigue, in fibromyalgia and related conditions, in irritable bowel syndrome and in relieving the general fatigue and neurological symptoms which are seen not just in MS but in almost any illness which involves any form of damage to the brain or spinal cord.

Case History No. 1

An example of the use of our invention was a woman of 41 years of age who had been incapacitated for about 12 years by chronic fatigue syndrome associated with fibromyalgia and irritable bowel syndrome. Until the age of 29 she had been a relatively normal woman, married with two children. However she then experienced what appeared to be a mild attack of influenza. Instead of recovering quickly as usual, she became depressed and fatigued and unable to carry out her normal parttime work and care for her children in the usual way. Everything became an effort and she could sustain only short bursts of activity before having to rest. She also developed multiple aches and pains throughout her body, characteristic of fibromyalgia, and an irritable bowel in which painful spasms alternated with constipation. She was given almost all conceivable treatments over the years, including many types of non-steroidal anti-inflammatory drugs, both tricyclic and serotonin reuptake inhibiting and noradrenaline reuptake inhibiting antidepressants, and even steroids. Some of these treatments produced transient effects but these never lasted. She was then given combined treatment with lofepramine, 70 mg bd and L-phenylalanine, 500 mg bd. Over a period of 2–3 weeks she experienced a considerable improvement in fatigue, in fibromyalgia and in her irritable bowel. She and her family expected these effects to wear off but instead they persisted. After six months she was essentially back to her normal self.

The implications are important in stroke and brain injury which have remained depressingly resistant to the development of pharmacological interventions. Many recent trials of a wide variety of agents have failed to alter the outcome in stroke or brain injury. However, there are animal studies which are encouraging in this respect. In essence, experimental stroke is associated with inhibition of LC function and the generalised loss of motor function appears to be caused by a failure of the noradrenergic system (Boyeson et al and Feeney et al, above). Treatment with noradrenaline facilitates recovery in animals from such lesions and there is preliminary evidence that there may be beneficial effects in humans (Feeney et al and Boyeson et al, above and also, D M Feeney, From laboratory to clinic: noradrenergic enhancement of physical therapy for stroke or trauma patients. Brain Plasticity: Advances in Neurology 1997; 73: 383–394. M G Boyeson and K A Krobert, Cerebellar norepinephrine infusions facilitate recovery after sensorimotor cortex injury, Brain Research Bulletin 1992; 29: 435–439. M G Boyeson & D M Feeney, Intraventricular norepinephrine facilitates motor recovery following sensorimotor cortex injury. Pharmacology Biochemistry and Behavior 1990; 35: 497–501). Of particular interest, desipramine, which is a metabolite of lofepramine, is able to enhance LC function and recovery of motor function after brain lesions: in contrast, drugs acting on the serotonin system have much smaller effects. (M G Boyeson & R L Harmon, Effects of trazodone and desipramine on motor recovery in brain-injured rats. American Journal of Physical Medicine and Rehabilitation 1993; 72: 286–293. R J Valentino et al, Antidepressant actions on brain noradrenergic neurons. Journal of Pharmacology and Experimental therapeutics 1990; 253: 833–840. M G Boyeson et al. Comparative effects of fluoxetine, amitriptyline and serotonin on functional motor recovery after sensorimotor cortex injury. American Journal of Physical Medicine and Rehabilitation 1994; 73: 76–83).

These effects of noradrenergic compounds alone are important but relatively modest. Our concept of combining a noradrenergic drug like lofepramine or desipramine, together with a noradrenaline precursor such as phenylalanine or tyrosine, is much more effective. This is surprising because many people have tried to enhance noradrenaline synthesis by administering the precursors phenylalanine or tyrosine but have failed. Many studies have shown that in normal humans and animals the administration of phenylalanine or tyrosine has little or no effect on the synthesis of noradrenaline (J D Milner and R J Wurtman, Catecholamine synthesis: physiological coupling to precursor supply. Biochemical Pharmacology 1986; 35: 875–881.) As the Milner & Wurtman paper demonstrates, there is a very good reason for this: the end product of the reaction sequence, noradrenaline, feeds back to strongly inhibit the activity of tyrosine hydroxylase, a key rate-limiting enzyme in the synthesis of noradrenaline. As a result, under normal circumstances providing phenylalanine or tyrosine will not influence noradrenaline production to any substantial degree. However, the situation changes when noradrenergic systems are activated or stressed. Under these circumstances tyrosine hydroxylase becomes phosphorylated and resistant to feedback inhibition by noradrenaline. As a result, in this situation the administration of phenylalanine or tyrosine does indeed activate noradrenaline synthesis (Milner and Wurtman). We propose that this is the explanation for the strong interaction we have observed between lofepramine and phenylalanine. In MS, the LC and LT noradrenergic systems are activated and stressed leading to loss of the feedback control of noradrenaline synthesis. As a result phenylalanine can enhance noradrenaline synthesis and strongly interact with lofepramine which inhibits uptake of released noradrenaline and so activates noradrenergic systems. We propose that a similar release of feedback inhibition occurs in any situation of brain injury, brain viral or other infections, including bacterial and prion infections, or chronic stress and that as a result the combination of a noradrenaline precursor and a noradrenergic drug will be beneficial in fatigue of any sort including fatigue after stroke, brain injury, migraine, MS, viral and other infections and chronic stress. We also suggest that the combination of a noradrenaline precursor and a noradrenergic drug will substantially enhance the rate and the degree of recovery from stroke or other brain damage.

Case History No.2

An example of this treatment is that of a 65 year old man who was apparently healthy experienced a small stroke which temporarily led to some loss of function in his left arm and left. The major part of the deficit recovered within a matter of days and within about six months there was no evidence of any residual specific sensorimotor problem apart from slight left arm weakness. However, over the month or so following the initial stroke the man became seriously depressed and fatigued, a state which he had not experienced before. He found it difficult to summon the energy to do anything. He also experienced the classic signs of depression with an unduly gloomy view of the impact of the stroke on his future life, an inability to take interest in things which had previously been a major part of his life, a strong sense of guilt about not spending enough time with his family prior to the stroke, and early morning wakening. He was treated first with imipramine, then with fluoxetine and then with lofepramine without much success. Eventually 500 mg of L-phenylalanine taken twice daily in the morning and evening was added to his 70 mg bd dose of lofepramine. Within a week he began to fell better and within four weeks he appeared to be largely recovered. His energy had returned, he enjoyed his family and his view of his future prospects improved considerably. In this patient antidepressants alone were clearly inadequate to relieve either his depression or his fatigue but the addition of phenylalanine to lofepramine allowed resolution of most of his post-stroke problems.

MECHANISM

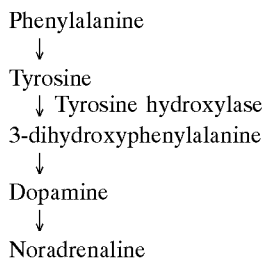

Phenylalanine
↓
Tyrosine
↓ Tyrosine hydroxylase
3-dihydroxyphenylalanine
↓
Dopamine
↓
Noradrenaline This unique mechanism thus activates the brain LC and LT systems particularly well when there is a need for activation as demonstrated by removal of the feedback inhibition of noradrenaline synthesis. In contrast, in normal situations when feedback inhibition is fully operative, the combination will not exert adverse effects because then the phenylalanine or tyrosine will not be able to enhance noradrenaline synthesis. Because of a failure to understand this unique mechanism, although it has been proposed that phenylalanine and tyrosine may be used to treat depression, it has never been proposed that phenylalanine or tyrosine should be specifically combined with drugs which have specific effects on noradrenaline reuptake such as lofepramine, desipramine and reboxetine. Such combinations will be particularly effective in treating depression, especially when that depression is associated with chronic stress and abnormal function of the LC and LT systems.

The drugs which are most effective in the combination are those which have a large effect on the reuptake of noradrenaline at nerve endings and which at the same time have little effect or a much smaller effect on the uptake of serotonin. This can be demonstrated by studying the actions of the drugs on systems such as rat brain synaptosomes (C Bolden-Watson and E. Richelson, Blockade by newly developed antidepressants of biogenic amine uptake into rat brain synaptosomes. Life Sciences 1993; 52: 1023–1029. C Sanchez and J Hyttel, Comparison of the effects of antidepressants and their metabolites on reuptake of biogenic amines and on receptor binding. Cellular and Molecular Neurobiology 1999; 19: 467–489). The most effective compounds will have a large effect on noradrenaline which is at the same time at least ten times larger than their effect on serotonin. Drugs which fall into this class include lofepramine, desipramine (also known as desmethylimipramine), nortriptyline, tomoxetine, maprotiline, oxaprotiline, levoprotiline, viloxazine and reboxetine. A second class of drugs which will have effects but which will be less active in selectively activating the LC and LT systems are the drugs which have combined actions on noradrenaline and serotonin reuptake or on noradrenaline and dopamine uptake. These drugs include venlafaxine, duloxetine, buproprion and milnacipran.

The key precursors which will be effective in a way which is appropriate to the state of the noradrenergic systems are the amino acids on the noradrenaline synthesis pathway which are before the rate-limiting regulated step of tyrosine hydroxylase. This means L-phenylalanine and L-tyrosine. The D forms of these amino acids may also have some activity since there is some recent evidence that they can be converted into the L-forms which are the specific noradrenaline precursors by enzymes which are present in the brain.

The noradrenergic drug and the precursor may be formulated together in the same dosage form or may be presented in separate dosage forms but in the same pack using methods familiar to those skilled in the art. The dosage forms may include tablets, coated tablets, hard or soft gelatin capsules, liquids, gels, creams, suppositories, pessaries and parenteral formulations.

Because there is recent evidence that many people with chronic depression, chronic fatigue or chronic stress, or with brain damage of any sort may have inadequate levels of essential nutrients, the combinations may also be formulated with appropriate essential nutrients. Nutrients which are particularly important in brain function include folic acid, vitamin B12, vitamin B6 and tetrahydrobiopterin and related compounds.

EXAMPLES

1. Tablets or capsules containing 50–100 mg of lofepramine together with 100 mg to 1000 mg of phenylalanine, one to four to be taken each day.
2. As (1) but in which the lofepramine and phenylalanine are presented in separate dosage forms.
3. Tablets or capsules containing 50–100 mg desipramine together with 100 mg to 1000 mg of phenylalanine, one to four to be taken each day.
4. As (3) but in which the desipramine and phenylalanine are presented in separate dosage forms.
5. Tablets or capsules containing 2–5 mg of reboxetine, together with 100 mg to 1000 mg of phenylalanine, one to four to be taken each day.

6. As (5) but in which the reboxetine and phenylalanine are presented in separate dosage forms.
7–12. As 1–6 but in which the amino acid is tyrosine instead of phenylalanine.
13. As 1–12 but in which the noradrenergic drug is any other selective noradrenaline reuptake inhibitor.
14. As 1–12 but in which the drug is a compound which inhibits both noradrenaline and serotonin reuptake such as venlafaxine or milnacipram.

It will be appreciated that the formulations and treatments used according to the present invention are directed to the alleviation of the conditions specified hereinbefore independently of the presence of multiple sclerosis. However, they are of primary use in the treatment of patients who suffer from these conditions in the absence of multiple sclerosis.

What is claimed is:

1. A method of treating a condition of fatigue associated with chronic fatigue syndrome, depression, brain infection strokes, stress, fibromyalgia, or irritable bowel syndrome, which method comprises administering to a patient in need thereof a pharmaceutically effective amount of a composition comprising a selective inhibitor of noradrenaline reuptake and either L-phenylalanine or tyrosine in the same dosage form or the same pack.

2. The method according to claim 1, wherein said fatigue is due to chronic fatigue syndrome, fibromyalgia, or brain infection.

3. The method according to claim 1, wherein said condition is associated with chronic fatigue syndrome, fibromyalgia, or irritable bowel syndrome.

4. The method according to claim 1, wherein said condition is associated with stress.

5. The method according to claim 1, wherein said selective inhibitor of noradrenaline reuptake is selected from lofepramine, desipramine and reboxetine.

6. The method according to claim 5, wherein said composition is formulated to provide from 50 to 1000 mg of lofepramine or desipramine, and from 100 to 1000 mg of L-phenylalanine or tyrosine as a unit dose to be taken from 1 to 4 times daily.

7. The method according to claim 5, wherein said composition is formulated to provide from 2 to 5 mg of reboxetine and from 100 to 1000 mg of L-phenylalanine or tyrosine as a unit dose to be taken from 1 to 4 times daily.

8. The method according to claim 1, wherein said selective inhibitor is a combined inhibitor of both noradrenaline and serotonin reuptake, or an inhibitor of both noradrenaline and dopamine reuptake.

9. The method according to claim 1, wherein said composition further comprises other essential nutrients.

10. A method according to claim 8, wherein said combined inhibitor of both noradrenaline and serotonin reuptake is venlafaxine, duloxetine or milnacipran, or wherein said combined inhibitor of both noradrenaline and dopamine reuptake is buproprion.

11. A method according to claim 9, wherein said other essential nutrients are folic acid, vitamin B12, vitamin B6, or tetrahydrobiopterin.

12. The method according to claim 2, wherein said fatigue is due to brain infection with an agent, selected viruses, prions and bacteria.

* * * * *